(12) United States Patent
Carrico et al.

(10) Patent No.: US 6,359,049 B1
(45) Date of Patent: Mar. 19, 2002

(54) COLOR-STABLE SUPERABSORBENT POLYMER COMPOSITION

(75) Inventors: Peter W. Carrico, Columbus, MS (US); David Eckert, Gurnee, IL (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/523,345

(22) Filed: Mar. 10, 2000

Related U.S. Application Data

(60) Provisional application No. 60/123,958, filed on Mar. 12, 1999.

(51) Int. Cl.$^7$ .......................... C08L 33/02; C08L 39/00; C08L 39/02; C08L 3/32; A31F 13/15
(52) U.S. Cl. .................. 524/414; 524/556; 524/555; 524/548; 604/358; 604/372
(58) Field of Search .................... 524/414, 423, 524/556, 555, 548; 604/358, 367, 370, 372

(56) References Cited

U.S. PATENT DOCUMENTS

| | | | | |
|---|---|---|---|---|
| 4,769,414 A | * | 9/1988 | Kightlinger et al. | 525/54.24 |
| 5,115,011 A | * | 5/1992 | Herada et al. | 524/419 |
| 5,439,993 A | * | 8/1995 | Ito et al. | 526/93 |
| 5,599,335 A | | 2/1997 | Goldman et al. | 604/368 |
| 5,669,894 A | | 9/1997 | Goldman et al. | 604/368 |
| 5,773,542 A | * | 6/1998 | Koudate et al. | 526/215 |
| 5,981,689 A | * | 11/1999 | Mitchell et al. | 528/229 |
| 6,072,101 A | * | 6/2000 | Beihoffer et al. | 604/372 |

FOREIGN PATENT DOCUMENTS

| | | | |
|---|---|---|---|
| DE | 4127814 | * | 3/1992 |
| EP | 0 249 391 A2 | | 12/1987 |
| EP | 0 398 653 A1 | | 11/1990 |
| EP | 0 441 975 A1 | | 8/1991 |
| EP | 0 505 163 A1 | | 9/1992 |
| JP | 01039938 | * | 2/1989 |
| JP | 02289625 | * | 12/1990 |
| JP | 02311503 | * | 12/1990 |

OTHER PUBLICATIONS

English Translation of JP 02289625 (1990).*

* cited by examiner

*Primary Examiner*—Vasu Jagannathan
*Assistant Examiner*—Callie E Shosho
(74) *Attorney, Agent, or Firm*—Marshall, Gerstein, & Borun

(57) ABSTRACT

A color-stable superabsorbent polymer composition having long-term color stability, and methods of manufacturing the composition, are disclosed. The superabsorbent polymer composition contains an inorganic reducing agent and an optional metal salt, and resists color degradation during periods of extended storage, even at an elevated temperature and humidity.

20 Claims, No Drawings

COLOR-STABLE SUPERABSORBENT POLYMER COMPOSITION

CROSS-REFERENCE TO RELATED APPLICATION

This application claims the benefit of provisional patent application Serial No. 60/123,958, filed Mar. 12, 1999.

FIELD OF THE INVENTION

The present invention generally relates to superabsorbent polymer (SAP) compositions having long-term color stability. The color-stable SAP compositions can be incorporated into articles, such as bandages, diapers, sanitary napkins, and other disposable paper products, wherein the SAP composition retains a clean, white color during extended storage periods, even under high temperature and humidity conditions.

BACKGROUND OF THE INVENTION

Water-absorbing resins are widely used in sanitary and hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are discussed generally in Goldman et al. U.S. Pat. Nos. 5,669,894 and 5,559,335, the disclosures of which are incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

As used herein, the term "SAP particles" refers to superabsorbent polymer particles in the dry state, more specifically, particles containing from no water up to an amount of water less than the weight of the particles. The terms "SAP gel," "SAP hydrogel," or "hydrogel" refer to a superabsorbent polymer in the hydrated state, more specifically, particles that have absorbed at least their weight in water, and typically several times their weight in water.

SAPs have a tendency to degrade in color after long periods of storage. The tendency of an SAP to undergo a color transition from a clean, crisp, white color to a honey brown color accelerates as storage time, temperature, and humidity increases. In temperate climates, such as the United States and Europe, the rate at which an SAP undergoes color degradation is sufficiently slow such that the SAP, or article containing the SAP, typically is consumed before a color change is observable to the naked eye.

However, in tropical and subtropical climates, SAP color degradation is sufficiently rapid such that a color change often occurs before the SAP, or article containing the SAP, is consumed. In areas like southeast Asia, an SAP can change color from white to honey brown in about 4 to 6 weeks. This problem is exacerbated because the SAPs are produced far from the tropical climate, thereby increasing the time span of from SAP production to use. Furthermore, consumption of articles containing an SAP in such climates is relatively low, therefore further increasing the time period between SAP production and use.

The change in color of the SAP does not affect SAP performance, but adversely affects consumer acceptance of articles containing the color-degraded SAPs. In particular, consumers observing a color-degraded SAP in a diaper form an opinion that the diaper contains a contaminant, is somehow soiled or faulty, or is of low quality. The diaper typically is returned for a refund, and the consumer is less likely to repurchase that brand of diaper.

Problems also arise at the manufacturing level because manufacturers of diapers and other articles containing an SAP refuse to incorporate a discolored SAP into their products, and return the discolored SAP to the SAP manufacturer. A color-degraded SAP, therefore, ultimately adversely affects the manufacturer of articles and the manufacturer of the SAP, who must absorb the cost of the returned goods.

It would be desirable to provide an SAP that exhibits exceptional color stability properties, such that the SAP retains its crisp, white color throughout the useful life of the SAP, or the article containing the SAP, even when stored under high temperature and humidity conditions. Furthermore, it would be desirable to provide an SAP having a long-term color stability, without adversely affecting the absorbent properties of the SAP, such as absorbing a large amount of liquids quickly, having a good fluid permeability into and through the SAP, and having a high gel strength, such that a hydrogel formed from the SAP does not deform or flow under an applied stress or pressure.

SUMMARY OF THE INVENTION

The present invention is directed to an superabsorbent polymer (SAP) composition having long-term color stability, and to methods of manufacturing a color-stable SAP composition. More particularly, the present invention is directed to a color-stable SAP composition that retains its crisp, clean white color over an extended storage period at a high temperature and humidity, i.e., at least six (6) months when stored at 60° C. and 75% relative humidity.

One aspect of the present invention, therefore, is to provide a color-stable SAP composition comprising an SAP, about 0.05 to about 5 mole % of an inorganic reducing agent, and 0% to about 5 mole % of a metal salt, each mole % based on the total amount of monomers in the composition. When a metal salt is present, the metal salt and inorganic reducing agent are present in a mole ratio of about 3 to 1 to about 1 to 3, respectively.

Another aspect of the present invention is to provide a method of manufacturing a color-stable SAP composition, including the steps of polymerizing a monomer that provides an SAP, like an $\alpha,\beta$-unsaturated carboxylic acid, such as acrylic acid, either neutralized, unneutralized, or partially neutralized, to form a polymeric hydrogel, admixing an inorganic reducing agent and an optional metal salt into the hydrogel, and then drying the resulting admixture to form a color-stable SAP composition. The resulting color-stable SAP composition has the color-stabilizing compounds homogeneously dispersed throughout the SAP.

Another aspect of the invention is to provide a method of manufacturing a color-stable SAP composition including the steps of polymerizing a monomer that provides an SAP, for example, an α,β-unsaturated carboxylic acid (either neutralized, unneutralized, or partially neutralized), to form a polymeric hydrogel, drying the hydrogel to form SAP particles, and then adding the inorganic reducing agent and optional metal salt to the SAP particles to provide a color-stable SAP composition. The color-stabilizing compounds can be added to the SAP particles by applying one or more solutions of the color-stabilizing compounds to the SAP particles. The color-stabilizing compounds also can be added to the SAP particles by admixing SAP particles with solid particles of the color-stabilizing compounds. The color-stabilizing compounds can be added to the SAP particles individually, or together, or in conjunction with a surface treatment that provides surface crosslinks on the SAP particle.

In another aspect of the present invention, the color-stabilizing compounds can be added to the SAP during manufacture of the SAP particles to prevent discoloration. The color-stabilizing compounds also can be added to previously prepared SAP particles to prevent any additional discoloration of the SAP particles.

In accordance with another aspect of the present invention, a color-stable SAP composition can be incorporated into articles used to absorb liquids, like diapers and catamenial devices. The articles resist color degradation over the expected life of the article, even in high temperature and humidity climates.

The above and other aspects and advantages of the present invention will become apparent from the following detailed description of the preferred embodiments of the invention, taken in conjunction with the examples and the claims.

DETAILED DESCRIPTION OF THE INVENTION

The present invention is directed to an SAP composition having long-term color stability. The color-stable SAP compositions contain a sufficient amount of an inorganic reducing agent and an optional metal salt such that the SAP compositions resist an observable color change, to the naked eye, after storage for at least six months at 60° C. and 75% relative humidity. The present color-stable SAP compositions, after incorporation into a diaper, change in color less than 10 Gardner units after storing the diaper for eight weeks at 60° C. and 95% relative humidity. The color-stable SAP compositions contain about 0.05 to about 5 mole % of an inorganic reducing agent and 0 to about 5 mole % of a metal salt, based on the amount of SAP in the composition.

In one embodiment, a color-stable SAP composition is prepared by a method comprising the steps of polymerizing a solution of a monomer capable of providing an SAP polymer, like an α,β-unsaturated carboxylic acid, such as acrylic acid, either neutralized, unneutralized, or partially neutralized, to form a polymeric hydrogel, admixing the inorganic reducing agent and optional metal salt with the polymeric hydrogel to disperse the color-stabilizing compounds in the hydrogel, preferably homogeneously, and then drying the resulting admixture to form a color-stable SAP composition.

Alternatively, a color-stable SAP composition is prepared by a method including the steps of polymerizing, for example, an α,β-unsaturated carboxylic acid, either neutralized, unneutralized, or partially neutralized, to form a polymeric hydrogel, then drying the hydrogel to form SAP particles. The inorganic reducing agent and optional metal salt, together or individually, then are added to the SAP particles to provide a color-stable SAP composition. The inorganic reducing agent and optional metal salt typically are applied as a spray from a solution or solutions containing one or both of the compounds. Solid particles, preferably a powder, of the inorganic reducing agent and optional metal salt, together or individually, also can be admixed with the SAP particles. The inorganic reducing agent and optional metal salt also can be applied to the SAP particles in conjunction with a surface crosslinking agent that often is applied to an SAP to improve the fluid absorption and retention properties of the SAP.

The color-stabilizing compounds also can be added to SAP particles before the particles are incorporated into an article of manufacture. The addition of color-stabilizing compounds prevents future discoloration of the SAP particles.

The present color-stable SAP compositions are based on monomers, particularly α,β-unsaturated carboxylic acids, that, after polymerization, have the ability to absorb several times their weight of a liquid. The remainder of the specification is directed to a color-stable SAP composition based on acrylic acid, however, other monomers, and especially other α,β-unsaturated carboxylic acids, can be used as the SAP in the color-stable SAP compositions of the present invention. The color-stable SAP compositions prepared by the present methods exhibit improved color stability regardless of the identity of the monomers used to prepare the SAP, and particularly SAPs based on an α,β-unsaturated carboxylic acid.

The identity of the SAP utilized in the present invention is not limited. The SAPs are prepared by methods well known in the art, for example, solution or emulsion polymerization. The SAPs, therefore, can comprise an acidic water-absorbing resin, a basic water-absorbing resin, a blend of an acidic and basic water-absorbing resin, or a multicomponent SAP particle as disclosed in WO 99/25393, the disclosure of which is incorporated herein by reference.

The SAPs are prepared, for example, by:

(1) copolymerizing a monomer and a cross-linking monomer in aqueous solution, and drying the resulting gel-like hydrous polymer by heating;

(2) dispersing an aqueous solution of acrylic acid and/or an alkali metal acrylate, a water-soluble radical polymerization initiator, and a crosslinkable monomer in an alicyclic and/or an aliphatic hydrocarbon solvent in the presence of a surface-active agent, and subjecting the mixture to suspension polymerization;

(3) saponifying copolymers of vinyl esters and ethylenically unsaturated carboxylic acids or their derivatives;

(4) polymerizing starch and/or cellulose, a monomer having a carboxyl group or capable of forming a carboxyl group upon hydrolysis, and a crosslinking monomer in an aqueous medium, and, as required, hydrolyzing the resulting polymer; or (5) reacting an alkaline substance with a maleic anhydride-type copolymer containing maleic anhydride and at least one other monomer, and, as required, reacting the reaction product with a polyepoxy compound. Other methods and monomers that provide SAPs also are known in the art.

Generally, acidic SAPs have carboxylate, sulfonate, sulfate, and/or phosphate groups incorporated along the polymer chain. Polymers containing these acid moieties are synthesized either from monomers previously substituted with one or more of these acidic functional groups or by incorporating the acidic functional group into the polymer after synthesis. To incorporate carboxyl groups into a polymer, any of a number of ethylenically unsaturated carboxylic acids can be homopolymerized or copolymerized. Carboxyl groups also can be incorporated into the polymer chain indirectly by hydrolyzing a homopolymer or copolymer of monomers such as acrylamide, acrylonitrile, methacrylamide, and alkyl acrylates or methacrylates.

An acidic SAP can be either a strong or a weak acidic water-absorbing resin. The SAP can be a single resin, or a mixture of resins. The SAP can be a homopolymer or a copolymer.

The acidic SAP typically is a neutralized, lightly crosslinked acrylic-type resin, such as neutralized, lightly crosslinked polyacrylic acid. The lightly crosslinked acidic SAP typically is prepared by polymerizing an acidic monomer containing an acyl moiety, e.g., acrylic acid, or a moiety capable of providing an acid group, i.e., acrylonitrile, in the presence of a free radical cross-linker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic SAP contains at least 50%, and more preferably, at least 75%, and up to 100%, acidic monomer units. The acidic resin can be unneutralized or neutralized, preferably neutralized at least 50 mole %, and most preferably at least 70 mole %, with a base prior to surface crosslinking.

Ethylenically unsaturated carboxylic acid and carboxylic acid anhydride monomers, and salts, useful in the acidic SAP include acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, 2-methyl-2-butene dicarboxylic acid, maleamic acid, N-phenyl maleamide, maleamide, maleic anhydride, fumaric anhydride, itaconic anhydride, citraconic anhydride, mesaconic anhydride, methyl itaconic anhydride, ethyl maleic anhydride, diethylmaleate, methylmaleate, and maleic anhydride.

Sulfonate-containing acidic SAPs can be prepared from monomers containing functional groups hydrolyzable to the sulfonic acid form, for example, alkenyl sulfonic acid compounds and sulfoalkylacrylate compounds. Ethylenically unsaturated sulfonic acid monomers include aliphatic or aromatic vinyl sulfonic acids, such as vinylsulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, 2-vinyl-4-ethylbenzene, 2-allylbenzene sulfonic acid, 1-phenylethylene sulfonic acid, sulfopropyl methacrylate, 2-hydroxy-3-methacryloxypropyl sulfonic acid, and 2-acrylamide-2-methylpropane sulfonic acid.

Sulfate-containing acidic SAPs are prepared by reacting homopolymers or copolymers containing hydroxyl groups or residual ethylenic unsaturation with sulfuric acid or sulfur trioxide. Examples of such treated polymers include sulfated polyvinylalcohol, sulfated hydroxyethyl acrylate, and sulfated hydroxypropyl methacrylate. Phosphate-containing acidic SAPs are prepared by homopolymerizing or copolymerizing ethylenically unsaturated monomers containing a phosphoric acid moiety, such as methacryloxy ethyl phosphate.

Copolymerizable monomers for introduction into the acidic SAP, or into a basic SAP, include, but are not limited to, ethylene, propylene, isobutylene, $C_1$ to $C_4$ alkyl acrylates and methacrylates, vinyl acetate, methyl vinyl ether, and styrenic compounds having the formula:

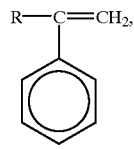

wherein R represents hydrogen or a $C_{1-6}$ alkyl group, and wherein the phenyl ring optionally is substituted with one to four $C_{1-4}$ alkyl or hydroxy groups.

Suitable $C_1$ to $C_4$ alkyl acrylates include, but are not limited to, methyl acrylate, ethyl acrylate, isopropyl acrylate, n-propyl acrylate, n-butyl acrylate, and the like, and mixtures thereof. Suitable $C_1$ to $C_4$ alkyl methacrylates include, but are not limited to, methyl methacrylate, ethyl methacrylate, isopropyl methacrylate, n-propylmethylmethacrylate, n-butyl methacrylate, and the like, and mixtures thereof or with $C_{1-4}$ alkyl acrylates. Suitable styrenic compounds include, but are not limited to, styrene, α-methylstyrene, p-methylstyrene, t-butyl styrene, and the like, and mixtures thereof or with $C_{1-4}$ alkyl acrylates and/or methacrylates.

As set forth above, polymerization of acidic monomers, and optional copolymerizable monomers, most commonly is performed by free radical processes in the presence of a polyfunctional organic compound. The acidic SAPs are crosslinked to a sufficient extent such that the polymer is water insoluble. Crosslinking renders the SAPs substantially water insoluble, and, in part, serves to determine the absorption capacity of the SAPs. For use in absorption applications, an acidic SAP is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters represented by the following formula (I); and bisacrylamides, represented by the following formula (II).

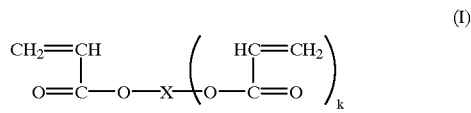

(I)

wherein X is ethylene, propylene, trimethylene, cyclohexyl, hexamethylene, 2-hydroxypropylene, —(CH$_2$CH$_2$O)$_p$CH$_2$CH$_2$—, or

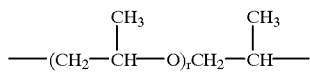

p and r are each an integer 5 to 40, and k is 1 or 2;

(II)

wherein 1 is 2 or 3.

The compounds of formula (I) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (II) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl)isocyanurate triacrylate, tris(2-hydroxyethy)isocyanurate trimethacrylate, divinyl esters of a polycarboxylic acid, diallyl esters or a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used. Especially preferred crosslinking agents are N,N'-methylenebisacrylamide, N,N'-methylenebismethacrylamide, ethylene glycol dimethacrylate, and trimethylolpropane triacrylate.

The acidic SAP, either strongly acidic or weakly acidic, can be any resin that acts as an SAP in its neutralized form. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The acidic SAP contains from 0 to 100 percent neutralized pendant carboxylate groups. Neutralization of carboxylic acid groups is accomplished using a strong organic or inorganic base, such as sodium hydroxide, potassium hydroxide, ammonia, ammonium hydroxide, or an organic amine.

Analogous to the acidic SAP, a basic SAP can be used in the present color-stable SAP compositions. The basic SAP can be a strong or weak basic water-absorbing resins. The strong basic resins typically are present in the hydroxide (OH) or bicarbonate (HCO$_3$) form. The basic SAP can be a single resin or a mixture of resins. The basic SAP can be a homopolymer or a copolymer.

The basic SAP typically is a lightly crosslinked acrylic-type resin, such as a poly(vinylamine). The basic resin also can be a polymer such as a lightly crosslinked polyethylenimine, a poly(allylamine), a poly(allylguanidine), a poly(dimethyldiallylammonium hydroxide), a quaternized polystyrene derivative, such as

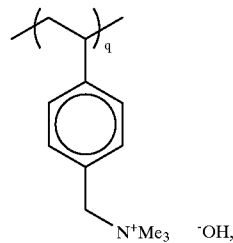

a guanidine-modified polystyrene, such as

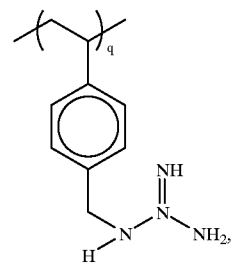

a quaternized poly((meth)acrylamide) or ester analog, such as

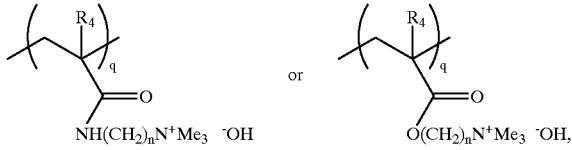

wherein Me is methyl, $R_4$ is hydrogen or methyl, n is a number 1 to 8, and q is a number from 10 to about 100,000, or a poly(vinylguanidine), i.e., poly(VG), a strong basic water-absorbing resin having the general structural formula

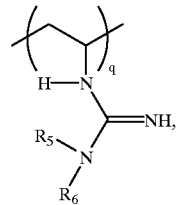

wherein q is a number from 10 to about 100,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, naphthyl, and similar aliphatic and aromatic groups. The lightly crosslinked basic SAP can contain other copolymerizable units and is crosslinked using a polyfunctional organic compound, as set forth above with respect to the acidic SAP.

A basic SAP used in the present SAP composition typically contains an amino or a guanidine group. Accordingly, a water-soluble basic resin can be crosslinked in solution by suspending or dissolving an uncrosslinked basic resin in an aqueous or alcoholic medium, then adding a di- or polyfunctional compound capable of crosslinking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $ZS(O_2)O—(CH_2)_n—OF(O)_2Z$, wherein n is 1 to 10, and Z is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate or methylene diisocyanate). Crosslinking agents for basic resins also are disclosed in Pinschmidt, Jr. et al. U.S. Pat. No. 5,085,787, incorporated herein by reference, and in EP 450 923.

Conventionally, the crosslinking agent is water or alcohol soluble, and possesses sufficient reactivity with the basic resin such that crosslinking occurs in a controlled fashion, preferably at a temperature of about 25° C. to about 150° C. Preferred crosslinking agents are ethylene glycol diglycidyl ether (EGDGE), a water-soluble diglycidyl ether, and a dibromoalkane, an alcohol-soluble compound.

The basic SAP, either strongly or weakly basic, therefore, can be any resin that acts as an SAP in its charged form. Examples of basic SAPs include a poly(vinylamine), a polyethylenimine, a poly(vinylguanidine), a poly (allylamine), a poly(allylguanidine), or a poly (dialkylaminoalkyl (meth)acrylamide) prepared by polymerizing and lightly crosslinking a monomer having the structure

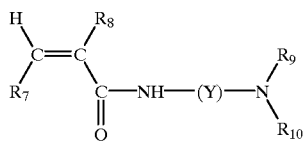

or its ester analog

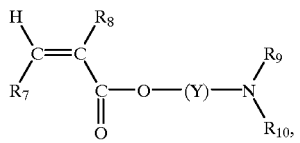

wherein $R_7$ and $R_8$, independently, are selected from the group consisting of hydrogen and methyl, Y is a divalent straight chain or branched organic radical having 1 to 8 carbon atoms, $R_9$ is hydrogen, and $R_{10}$ is hydrogen or an alkyl radical having 1 to 4 carbon atoms. Preferred basic SAPs include a poly(vinylamine), polyethylenimine, poly (vinylguanadine), poly(methylaminoethyl acrylamide), and poly(methylaminopropyl methacrylamide).

As previously stated, the present invention is not limited to SAPs based on acrylic acid, but preferably extends SAPs that include, but not limited to, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, and maleic anhydride. Acrylic acid, i.e., $CH_2=CHCO_2H$, is the most preferred α,β-unsaturated carboxylic acid.

The acrylic acid and/or other vinyl monomers are polymerized by standard free radical techniques. Then, in one embodiment, the inorganic reducing agent and optional metal salt are incorporated into the polyacrylic acid hydrogel in such a manner that the compounds are distributed, preferably homogeneously and uniformly, throughout the SAP hydrogel. More specifically, the color-stabilizing compounds are distributed throughout an SAP particle such that a cross section of a particle of the color-stable SAP composition reveals that there is a substantially equal amount of color-stabilizing compounds at or near the core of the SAP particle and at or near the surface of the color-stable SAP particle.

It should be understood, however, that a uniform distribution of the color-stabilizing compositions throughout a color-stable SAP particle is not required to impart color stability to the SAP. It is important, however, that the color-stabilizing compounds be present near the surface of the present SAP composition particles to retard or prevent color formation. Discoloration at the core of the SAP particle is acceptable because discoloration at the core cannot be observed by consumers, and discoloration does not adversely affect SAP performance.

Therefore, in another embodiment, the inorganic reducing agent and optional metal salt are applied to the surface of SAP particles, such that the color-stabilizing compounds are at or near the surface of the SAP particles. The color-stabilizing compounds typically are applied to the SAP surface by spraying a solution or solutions containing the color-stabilizing compounds onto the SAP particles. Alternatively, solid particles of the color-stabilizing compounds can be admixed with the SAP particles to position color-stabilizing compounds at the surface of the SAP particles.

In either embodiment, the inorganic reducing agent and optional metal salt impart color stability to the SAP such that the color-stable SAP particles maintain a clean, white color, i.e., resist an observable color transition, to the naked eye, for at least six months after storage at 60° C. and 75% relative humidity.

A color-stable SAP composition of the present invention, after incorporation into a diaper and storage of the diaper at 60° C. and 90% relative humidity for eight weeks, exhibited a color change of less than about 6 Gardner units. Preferably, a present color-stable SAP composition incorporated into a diaper exhibits a color change of less than 10 Gardner units after eight weeks storage at 60° C. and 75% relative humidity, and more preferably less than 8 Gardner units.

After storage at 60° C. and 75% relative humidity for six months, a color-stable SAP composition of the present invention exhibited a decrease in HC60 color value of less than 8 units, and preferably less than 5 units. To achieve the full advantage of the present invention, the SAP composition exhibits a decrease in HC60 color value of less than 3 units.

In the preparation of a color-stable SAP composition of the present invention, the monomers, for example, α,β-unsaturated carboxylic acids, and especially, acrylic acid, are subjected to a polymerization reaction in the presence of a polymerization initiator and a crosslinker. The acrylic acid typically is neutralized about 50% to 100% prior to polymerization.

The α,β-unsaturated carboxylic acid, or other monomers, either neutralized or unneutralized, typically are provided as aqueous solutions which further contain a polymerization initiator and a crosslinker for the vinyl monomers. Any of the various polymerization initiators that are known for use in preparing SAPs can be used in the present invention. Examples of useful initiators are redox initiators comprising a reducing agent, such as a sulfite or bisulfite of an alkali metal, ammonium sulfite, ammonium metabisulfate, or ammonium bisulfite, a persulfate of an alkali metal or ammonium persulfate; t-butyl hydroperoxide; di-t-butyl hydroperoxide; t-butyl perbenzoate; t-butyl peroxy isopropyl carbonate; 1,1-di-t-butylperoxy-3,3,5-trimethylcyclohexane; benzoyl peroxide, dicumyl peroxide; caprylyl peroxide; sodium peracetate; and other redox initiators known to persons skilled in the art.

Examples of suitable thermal initiators include azobisisobutyronitrile; 4-t-butylazo-4'-cyanovaleric acid; 4,4'-azobis(4-cyanovaleric acid); 2,2'-azobis(2-amidinopropane) dihydrochloride; 2,2'-azobis(2,4-dimethylvaleronitrile); dimethyl 2,2'-azobisisobutyrate; 2,2'-azodimethyl bis(2,4-dimethylvaleronitrile); (1-phenylethyl) azodiphenylmethane; 2,2'-azobis(2-methylbutyronitrile); 1,1'-azobis(1-cyclohexanecarbonitrile); 2-(carbamoylazo) isobutyronitrile; 2,2'-azobis(2,4,4-trimethylpenta-2-phenylazo-2,4-dimethyl-4-methoxyvaleronitrile; 2,2'-azobis (2-methylpropane); 2,2'-azobis(N, N'dimethyleneisobutyramidine)dihydrochloride; 4,4'azobis (4-cyanopentanoic acid); 2,2'-azobis(2-methyl-N-[1,1-bis (hydroxymethyl)-2-hydroxyethyl]propionamide); 2,2'-azobis(2-methyl-N-[1,1-bis(hydroxymethyl)ethyl] propionamide); 2,2'-azobis[2-methyl-N(2-hydroxyethyl) propionamide]; 2,2'-azobis(isobutyramide)dihydrate; and other thermal initiators known to persons skilled in the art.

These initiators, redox and thermal, can be used singly or in suitable combination. Of these, especially preferred initiators are a redox initiator comprising ammonium persulfate and sodium hydrogen sulfite, and azo initiators, such as azobisisobutyronitrile and 2,2'-azobis(2-amidinopropane) dihydrochloride. A suitable initiator for use in the invention is the azoinitiator 2,2'-azobis(2-amidinopropane) dihydrochloride, commercially available under the tradename V-50 from Wako Chemicals U.S.A., Inc., Richmond, Va. The initiator typically is used in an aqueous solution, but the initiator can be diluted with another suitable solvent. The initiator typically is used, for example, in an amount, calculated as solids, of about 0.1% to about 10%, and preferably about 0.5% to about 5%, based on the weight of the monomers. Depending on the amount and identity of the initiator, the initiator optionally can be used together with isopropyl alcohol, an alkyl mercaptan, or other chain transfer agent to control the molecular weight of the SAP.

Ultraviolet (UV) light also can be used to effect polymerization of the acrylic acid. UV light can be used in conjunction with a redox initiator and/or a free radical initiator. When UV light is utilized in the polymerization step, a photoinitiator also is added to the monomer mixture. The photoinitiator is used in a standard amount well known to persons skilled in the art. Suitable photoinitiators include, but are not limited to, 2-hydroxy-1-[4-(hydroxyethyoxy) phenyl]-2-methyl-1-propanone, which is commercially available from Ciba Additives of Hawthorne, N.Y., as IRGACURE 2959, and 2-hydroxy-2-methyl-1-phenyl-1-propanone which also is commercially available from Ciba Additives as DAROCUR 1173.

The acrylic acid monomer, or salt thereof, is crosslinked concurrently with aqueous solution polymerization to a sufficient extent such that the resulting polymer is water insoluble, but has an ability to absorb several times its weight in water to form a hydrogel. Crosslinking therefore renders the resulting polymer substantially water-insoluble and, in part, serves to determine the absorption capacity of the SAP. For use in absorption applications, the SAP is lightly crosslinked. The amount and identity of crosslinking agents used in the preparation of an SAP are discussed above.

In many cases, the SAP is surface treated. Surface treatment results in surface crosslinking of the particle. Surface treating an SAP enhances the ability of the SAP to absorb and retain aqueous media under a load.

As understood in the art, a surface-crosslinked SAP has a higher level of crosslinking in the vicinity of the surface than in the interior. As used herein, "surface" describes the outer-facing boundaries of the SAP particle. For porous SAP particles, exposed internal surface also is included in the definition of surface.

As described hereafter, the inorganic reducing agent and optional metal salt can be applied to the SAP in conjunction with surface crosslinking of the SAP. In general, surface crosslinking is achieved by contacting an SAP with a solution of a surface crosslinking agent to wet the outer surfaces of the SAP particles. Surface crosslinking and drying of the SAP particles then is performed, preferably by heating at least the wetted surfaces of the SAP particles.

Typically, SAP particles are surface treated with a solution of a surface crosslinking agent. The solution contains about 0.01% to about 4%, by weight, surface crosslinking agent, and preferably about 0.4% to about 2%, by weight, surface crosslinking agent in a suitable solvent, for example, water or an alcohol. The solution can be applied as a fine spray onto the surface of freely tumbling SAP particles at a ratio of about 1:0.01 to about 1:0.5 parts by weight SAP particles to solution of surface crosslinking agent. The surface crosslinker is present in an amount of 0% to about 5%, by weight of the SAP particles, and preferably 0% to about 0.5% by weight. To achieve the full advantage of the present invention, the surface crosslinker is present in an amount of about 0.001% to about 0.1% by weight.

The crosslinking reaction and drying of the surface-treated SAP particles are achieved by heating the surface-treated polymer at a suitable temperature, e.g., about 25° C. to about 200° C., and preferably about 105° C. to about 120° C. However, any other method of reacting the crosslinking agent to achieve surface crosslinking of the SAP particles, and any other method of drying the SAP particles, such as microwave energy, or the such as can be used.

With respect to the SAP particles comprising an acidic resin (e.g., polyacrylic acid), suitable surface crosslinking agents are capable of reacting with carboxyl moieties and crosslinking the acidic resin. Preferably, the surface crosslinking agent is alcohol soluble or water soluble, and possesses sufficient reactivity with an acidic resin such that crosslinking occurs in a controlled fashion, preferably at a temperature of about 25° C. to about 150° C.

Nonlimiting examples of suitable surface crosslinking agents for acidic resins include:

(a) polyhydroxy compounds, such as glycols and glycerol;

(b) metal salts;

(c) quaternary ammonium compounds;

(d) a multifunctional epoxy compound;

(e) an alkylene carbonate, such as ethylene carbonate or propylene carbonate;

(f) a polyaziridine, such as 2,2-bis-hydroxymethyl butanol tris[3-(1-aziridine propionate]);

(g) a haloepoxy, such as epichlorhydrin;

(h) a polyamine, such as ethylenediamine;

(i) a polyisocyanate, such as 2,4-toluene diisocyanate; and (j) other crosslinking agents for acidic water-absorbing resins known to persons skilled in the art.

With respect to SAP particles comprising a basic resin, suitable surface crosslinking agents include di- or polyfunctional molecules capable of reacting with amino groups and crosslinking a basic resin. Preferably, the surface crosslinking agent is alcohol or water soluble and possesses sufficient reactivity with a basic resin, e.g., a polyvinylamine, such that crosslinking occurs in a controlled fashion at a temperature of about 25° C. to about 150° C.

Nonlimiting examples of suitable surface crosslinking agents for basic resins include:

(a) dihalides and disulfonate esters, for example, compounds of the formula $(Y-CH_2)_p-Y$, wherein p is a number from 2 to 12, and Y, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, such as epichlorohydrin;

(e) multifunctional epoxy compounds, for example, ethylene glycol diglycidyl ether, bisphenol A diglycidyl ether, and bisphenol F diglycidyl ether, (f) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, such as oxalic acid, adipic acid, succinic acid, dodecanoic acid, malonic acid, and glutaric acid, and esters, anhydrides, and acid chlorides derived therefrom;

(g) organic titanates, such as TYZOR AA, available from E. I. DuPont de Nemours, Wilmington, Del.;

(h) melamine resins, such as the CYMEL resins available from Cytec Industries, Wayne, N.J.;

(i) hydroxymethyl ureas, such as N,N'-dihydroxymethyl-4,5-dihydroxyethylene urea;

(j) multifunctional isocyanates, such as toluene diisocyanate, isophorone diisocyanate, methylene diisocyanate, xylene diisocyanate, and hexamethylene diisocyanate; and (k) other crosslinking agents for basic water-absorbing resins known to persons skilled in the art.

A particular surface crosslinking agent that can be used with an acidic or a basic SAP is a hydroxyalkylamide (HAA), for example, as disclosed in Swift et al. U.S. Pat. No. 4,076,917, incorporated herein by reference. An HAA has the following formula:

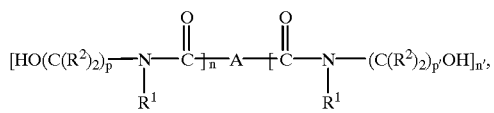

wherein A is a bond, hydrogen, or a monovalent polyvalent organic radical selected from the group consisting of a saturated or unsaturated alkyl radical contain 1 to 60 carbon atoms, such as methyl, ethyl, propyl, butyl, pentyl, hexyl, heptyl, octyl, nonyl, decyl, eicosyl, triacontyl, tetracontyl, pentacontyl, hexylcontyl, and the like, aryl, for example, mono- and dicyclic aryl, such as phenyl, naphthyl, and the like, tri-$C_{1-4}$ alkyleneamine, such as trimethyleneamino, triethyleneamino, and the like, and an unsaturated radical containing one or more ethylenic groups [>C=C<], such as ethenyl, 1-methylethenyl, 3-butenyl-1,3-diyl, 2-propenyl-1, 2-diyl, carboxy $C_{1-4}$ alkenyl, such as 3-carboxy-2-propenyl, and the like, $C_{1-4}$ alkoxy carbonyl lower alkenyl, such as 3-methoxycarbonyl-2-propenyl, and the like; $R^1$, selected independently, are hydrogen, straight or branched chain $C_{1-5}$ alkyl, such as methyl, ethyl, n-propyl, n-butyl, sec-butyl, tert-butyl, pentyl, and the like, or straight or branched chain $C_{1-5}$ hydroxyalkyl, such as hydroxyethyl, 3-hydroxypropyl, 2-hydroxypropyl, 4-hydroxybutyl, 3-hydroxybutyl, 2-hydroxy-2-methylpropyl, 5-hydroxypentyl, 4-hydroxypentyl, 3-hydroxypentyl, 2-hydroxypentyl, and the isomers of pentyl; $R^2$, selected independently, are radicals selected from the group consisting of hydrogen and straight or branched $C_{1-5}$ alkyl, or the $R^2$ radicals can be joined to form, together with the carbon atoms, a cycloalkyl ring, such as cyclopentyl, cyclohexyl, and the like; p and p', independently, are an integer 1 to 4; n is an integer having a value of 1 or 2, and n' is an integer having a value of 0 to 2, or when n' is 0, a polymer or copolymer (i.e., n has a value greater than 1, preferably 2–10) formed from the β-hydroxyalkylamide when A is an unsaturated radical.

Preferred HAAs are compounds wherein $R^1$ is H or $C_{1-5}$ hydroxyalkyl, n and n' are each 1, —A— is —$(CH_2)_m$—, m is 0–8, preferably 2–8, each $R^2$ on the α-carbon is H, and one of the $R^2$ radicals on the beta carbon in each case is H and the other is H or a $C_{1-5}$ alkyl, and q and q', independently, are an integer 1 to 3; that is,

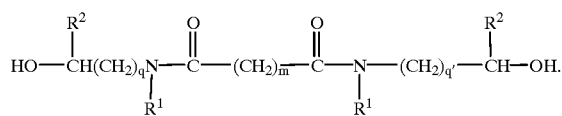

Most preferred HAAs have the formula:

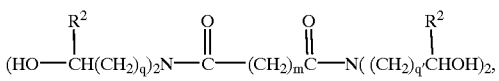

wherein both $R^2$ groups are H or both $R^2$ groups are —$CH_3$.

Specific examples of HAA compounds include, but are not limited to, bis[N,N-di(β-hydroxyethyl)] adipamide, bis[N,N-di(β-hydroxypropyl)] succinamide, bis[N,N-di(β-hydroxyethyl)] azelamide, bis[N-N-di(β-hydroxypropyl)] adipamide, and bis[N-methyl-N-(β-hydroxyethyl)] oxamide. A commercially available β-HAA is PRIMID™ XL-552 from EMS-CHEMIE, Dornat, Switzerland. PRIMID™ XL-522 has the structure

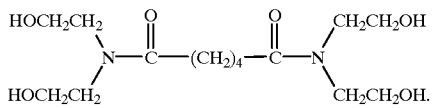

Another commercially available HAA is PRIMID™ QM-1260 from EMS-CHEMIE, having the structure:

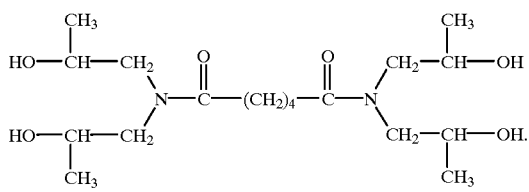

In another embodiment, the HAA has the cyclic structure

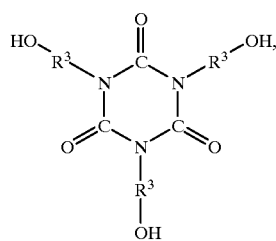

wherein $R^3$ is a divalent radical selected from the group consisting of an alkylene radical containing 1 to 4 carbon atoms and arylene. In preferred embodiments, $R^3$, independently, is $(CH_2)_2$, $(CH_2)_3$, or $$(CH_2CH) \atop CH_3.$$

A preferred surface crosslinking agent is an HAA, ethylene glycol, diglycidyl ether (EGDGE), or a mixture thereof, which crosslink a basic resin at a temperature of about 25° C. to about 150° C. Especially preferred surface crosslinking agents are an HAA and EGDGE.

The color-stable SAP compositions of the present invention also contain an inorganic reducing agent and an optional metal salt as color-stabilizing compounds. In accordance with an important feature of the prevent invention, the inorganic reducing agent and optional metal salt are added to the SAP to impart color stability to the SAP. In embodiments wherein color-stabilizing compounds are added to a hydrogel prior to extrusion, adding only one of the color-stabilizing compounds to the SAP fails to impart the desired color stability to the SAP.

It is theorized, but not relied upon herein, that inhibitors, which are added to the vinyl monomers to prevent premature polymerization during transport and storage, and which are present in the SAP polymer, are slowly oxidized and cause the color of the SAP to change from white to honey brown. This color change occurs at a faster rate at elevated temperatures and relative humidity.

For example, the monomethyl ether of hydroquinone (MEHQ) is the inhibitor typically used to prevent the premature polymerization of acrylic monomers used in the manufacture of the SAPs, like acrylic acid and the crosslinkers for acrylic acid. Typically, the amount of inhibitors, like MEHQ, added to the monomer is about 15 to about 200 ppm. The inhibitors are present in the SAP after polymerization of the monomers. The color change of the SAP is theorized to be oxidation of an inhibitor, like MEHQ, to a quinone.

To prevent the color transition of an SAP to a consumer-unacceptable honey brown color, about 0.05 to about 5 mole % of an inorganic reducing agent and 0 to 5 mole % of a metal salt are added to the SAP. Preferably, about 0.2 to about 3 mole % of each color-stabilizing compound is added to the SAP, based on the moles of vinyl monomer used to prepare the SAP. To achieve the full advantage of the present invention, each of the inorganic reducing agent and the metal salt is added to the SAP in an amount of about 0.50 to about 2.0 mole %.

In embodiments wherein a metal salt is present, for example, when the color-stabilizing compounds are added to a hydrogel prior to extrusion, the mole ratio of the inorganic reducing agent to metal salt is about 3 to 1 to about 1 to 3, and preferably about 2:1 to about 1:2. To achieve the full advantage of the present invention, the ratio of reducing agent to metal salt is about 1.5:1 to about 1:1.5.

The inorganic reducing agent typically is a hypophosphite, a phosphite, a bisulfite, or a sulfite salt. The cation of the reducing agent typically is sodium, potassium, or other Group I or Group II cation. Preferred reducing agents are sodium hypophosphite, sodium phosphite, sodium bisulfite, sodium sulfite, and mixtures thereof. The most preferred reducing agent is sodium hypophosphite. Other inorganic reducing agents known to persons skilled in the art also can be included in a color-stable SAP composition of the present invention.

The optional metal salt can contain a monovalent or polyvalent cation. A polyvalent cation is preferred. In addition, in preferred embodiments, the metal salt is water soluble. Water soluble is defined herein as metal salts having a water solubility of at least 3 grams (i.e., 3 grams or greater) in 100 milliliters (ml) of water at standard temperature and pressure, preferably at least about 5 grams per 100 ml of water, and more preferably at least about 7 grams per 100 ml of water.

The metal salt typically is an alkali or alkaline earth metal salt, i.e., a salt having a metal cation of valence I or II. The metal salt, however, also can contain a metal cation having a valence greater than II, such as a valence of III or IV. Therefore, the cation of the metal salt can be, for example, sodium, potassium, lithium, calcium, magnesium, aluminum, zinc, titanium, tin, bismuth, antimony, cerium, cobalt, lead, barium, manganese, iron, nickel, copper, similar monovalent and polyvalent metal cations, and mixtures thereof.

The anion of the metal salt typically is sulfate, but can be any other anionic moiety, either organic or inorganic in chemical structure, that assists or facilitates the inorganic reducing agent in performing its function. It has been found that if the anion is a halide, such as bromide or chloride, or nitrate, the inorganic reducing agent does not perform its color stabilizing function. Persons skilled in the art are capable of identifying other anions, like phosphate, acetate, lactate, or similar organic and/or inorganic anions, that are useful in the present invention.

Preferably, the optional metal salt is white in color. However, in applications where the SAP can be colored, a metal salt having color other than white can be used in the color-stable SAP composition. Mixtures of metal salts also can be used.

The inorganic reducing agent and optional metal salt are incorporated into the SAP composition after the SAP is prepared from the vinyl monomers. The reducing agent and metal salt are not added to the vinyl monomers prior to polymerization because the reducing agent can act as a chain transfer agent, and, therefore, can adversely affect the molecular weight of the SAP.

Accordingly, in one embodiment, the inorganic reducing agent and optional metal salt are added to a hydrogel of the SAP after polymerization of the vinyl monomers, and prior to drying the SAP hydrogel. In another embodiment, the inorganic reducing agent and optional metal salt are added to the SAP after the SAP is dried. The color-stabilizing compounds are added to the SAP, for example, by spraying a solution containing both compounds, or individual solutions of each compound, to the dried SAP particles, or by admixing solid particles of the color-stabilizing compounds with the SAP particles. In yet another embodiment, the polyvalent metal salt and inorganic reducing agent are applied to dried SAP particles in conjunction with the application of a surface crosslinker to the SAP particles. Each embodiment is illustrated hereafter in Examples 1–3.

In general, the monomers are polymerized to yield a highly-viscous hydrogel that is extruded, typically, onto a flat surface such as a continuously-moving conveyor belt. The inorganic reducing agent and optional metal salt can be admixed with the hydrogel prior to extruding. This admixture then can be extruded, and if not previously neutralized, can be neutralized with a base, for example, with sodium carbonate, to provide an extrudate having a degree of neutralization (DN) of about 50% to about 100%, preferably about 65% to about 85%, more preferably about 75% to about 80%. The extrudate also contains the color-stabilizing compounds. Drying of the extrudate provides a color-stable SAP composition of the present invention. In this embodiment, the metal salt is a necessary ingredient because admixing only an inorganic reducing agent with the hydrogel failed to provide sufficient color stabilization.

Alternatively, the viscous hydrogel is dehydrated (i.e., dried) to obtain an SAP in a solid or powder form. The dehydration step can be performed by heating the viscous hydrogel to a temperature of about 120° C. for about 1 to about 2 hours in a forced-air oven or by heating the viscous hydrogel overnight at a temperature of about 60° C. The dried SAP thereafter can be optionally surface crosslinked with a surface crosslinker, like ethylene glycol diglycidyl ether (i.e., "EGDGE") or an HAA, for example. The inorganic reducing agent and optional metal salt can be applied to the SAP particles either (a) as solutions to the surface of the dried SAP particles, (b) admixing solid particles (preferably in powder form) of the inorganic reducing agent and optional metal salt with the dried SAP particles, or (c) during application of the surface crosslinker.

The color-stable SAP compositions, therefore, either can have the inorganic reducing agent and optional metal salt distributed throughout the SAP particle, or present on the surfaces of the SAP particle, depending upon whether the color-stabilizing compounds are added to the hydrogel prior to extruding, or are added to the SAP after drying the hydrogel.

Particles of the color-stable SAP compositions of the present invention can be in any form, either regular or irregular, such as granules, fibers, beads, powders, flakes, or foams, or any other desired shape, such as a sheet. In embodiments wherein the color-stable SAP composition is prepared using an extrusion step, the shape of the SAP is determined by the shape of the extrusion die. The shape of the color-stable SAP particles also can be determined by other physical operations, such as milling.

In one embodiment, the particles of the color-stable SAP composition are in the form of a granule or a bead, having a particle size of about 10 to about 10,000 microns ($\mu$m), and preferably about 100 to about 1,000 $\mu$m. To achieve the full advantage of the present invention, the particles of the SAP composition have a particle size of about 150 to about 800 $\mu$m.

In another embodiment, the particles of the color-stable SAP composition are in the shape of a fiber, i.e., an elongated, acicular particle. The fiber can be in the shape of a cylinder, for example, having a minor dimension (i.e., diameter) and a major dimension (i.e., length). The fiber also can be in the form of a long filament that can be woven. Such filament-like fibers have a weight of below about 80 decitex, and preferably below about 70 decitex, per filament, for example, about 2 to about 60 decitex per filament. Tex is the weight in grams per one kilometer of fiber. One tex equals 10 decitex. Poly(acrylic acid) is about 4 decitex.

Cylindrical fibers of a color-stable SAP composition have a minor dimension (i.e., diameter of the fiber) less than about 1 mm, usually less than about 500 $\mu$m, and preferably less than 250 $\mu$m, down to about 50 $\mu$m. The cylindrical fibers can have a relatively short major dimension, for example, about 1 mm, e.g., in a fibrid, lamella, or flake-shaped article, but generally the fiber has a length of about 3 to about 100 mm. The filament-like fibers have a ratio of major dimension to minor dimension of at least 500 to 1, and preferably at least 1000 to 1, for example, up to and greater than 10,000 to 1.

A color-stable SAP composition has an outstanding water-absorbing ability, and is useful for use in sanitary goods, paper diapers, disposable diapers and similar hygienic goods, agricultural or horticultural water-retaining agents, industrial dehydrating agents, sludge coagulants, thickening agents, condensation preventing agents for building materials, release control agents for chemicals and various other applications. Furthermore, a present color-stable SAP composition retain s its white color over extended storage periods at elevated temperature and relative humidity. The present color-stable SAP composition, therefore, are useful in articles, like diapers, having improved consumer appeal.

EXAMPLES

The following illustrate nonlimiting examples of the present invention, and are not intended to limit the scope thereof.

Example 1

A monomer mixture containing about 25 to about 28 wt. % acrylic acid, 0.07 mole methylenebisacrylamide per mole of acrylic acid, 0.061 mole sodium persulfate per mole of acrylic acid, and about 72 to about 75 wt. % water was prepared. The resulting monomer mixture was polymerized under UV light for about 10 minutes. The polymerization was initiated using 0.017 mole DAROCUR 1173 per mole of acrylic acid. The resulting hydrogel was extruded, then treated with granular sodium carbonate to provide a neutralized hydrogel having a degree of neutralization (DN) of about 50% to about 100%.

To the resulting hydrogel was added a solution containing 2.9% by weight magnesium sulfate and 2.1% by weight sodium hypophosphite. The solution of color-stabilizing compounds was added while processing the hydrogel through an extruder. In this embodiment, the magnesium sulfate and sodium hypophosphite each was added to the hydrogel at a level of about 0.05 to about 5 mole %

(typically about 0.65 mole %), based on the amount of acrylic acid in the hydrogel to achieve sufficient color stabilization. Omitting the metal salt, like magnesium sulfate, adversely affects color stability in this type of embodiment. The resulting SAP hydrogel containing the color-stabilizing compounds then was further processed using conventional techniques to yield a color-stable SAP composition of the present invention. It is theorized that the addition of magnesium sulfate an d sodium hypophosphite to the SAP inhibits the oxidation of the MEHQ to various benzoquinones, which cause discoloration of the SAP.

Example 2

A monomer mixture containing about 25 to about 28 wt. % acrylic acid, 0.07 mole methylenebisacrylamide per mole of acrylic acid, 0.061 mole sodium persulfate per mole of acrylic acid, and about 72 to about 75 wt. % water was prepared. The resulting monomer mixture was polymerized under UV light for about 10 minutes. The polymerization was initiated using 0.017 mole DAROCUR 1173 per mole of acrylic acid. The resulting hydrogel was extruded, then treated with granular sodium carbonate to provide a neutralized hydrogel having a degree of neutralization (DN) of about 50% to about 100%. Next, the extruded hydrogel was dried in a forced-air oven at 120° C. for about 1 to 2 hours, then ground and sized through sieves to obtain a desired particle size. After drying and sizing, the SAP particles were surface crosslinked with 600 ppm of EGDGE.

To the surface-crosslinked SAP particles was applied an aqueous solution containing 11.6% by weight magnesium sulfate and 8.4% by weight sodium hypophosphite. The magnesium sulfate/sodium hypophosphite solution was applied to the SAP at a ratio of 1 to 15, based on the weight of the surface-crosslinked SAP. The amount of magnesium sulfate/sodium hypophosphite (present in a 1:1 molar ratio) added to the SAP was about 500 ppm to about 75,000 ppm. Optimum color-stabilizing results were observed at levels of color stabilizing compound above about 10,000 ppm, which corresponds to about 0.50 mole % of each color-stabilizing compound. The addition of the magnesium sulfate and sodium hypophosphite to the SAP prevented discoloration of the SAP over an extended storage period. However, the addition of magnesium sulfate, or any other metal salt, is optional because application of the inorganic reducing agent alone to the surface of the SAP effectively stabilized the color of the SAP.

Example 3

A monomer mixture containing about 25 to about 28 wt. % acrylic acid, 0.07 mole methylene-bisacrylamide per mole of acrylic acid, 0.061 mole sodium persulfate per mole of acrylic acid, and about 72 to about 75 wt. % water was prepared. The resulting monomer mixture was polymerized under UV light for about 10 minutes. The polymerization was initiated using 0.017 mole DAROCUR 1173 per mole of acrylic acid. The resulting hydrogel was extruded, then treated with granular sodium carbonate to provide a neutralized hydrogel having a degree of neutralization (DN) of about 50% to about 100%. The resulting extruded hydrogel was dried in a forced-air oven at a temperature of about 120° C. for about 1 to 2 hours, then ground and sized through sieves to obtain a desired particle size.

After drying and sizing, the color-stabilizing compounds were added to the SAP particles, and SAP particles were surface crosslinked with 600 ppm of EGDGE. In particular, the magnesium sulfate, sodium hypophosphite, and EGDGE were dispersed in a water/solvent solution. The solvent can be any water miscible solvent, such as an alcohol, a glycol, acetone, or tetrahydrofuran, for example. The resulting dispersion then was applied to the SAP, as a spray, at a ratio of 1 to 15, based on polymer weight. The resulting SAP then was heated to complete the surface crosslinking reaction. The amount of magnesium sulfate/sodium hypophosphite (combined in a 1:1 molar ratio) added to the SAP was identical to Example 2. The addition of the magnesium sulfate and sodium hypophosphite to the SAP prevented discoloration of the SAP over an extended period. Like Example 2, the presence of a metal salt is optional, because the inorganic reducing agent, alone, effectively stabilized the color of the SAP.

To demonstrate the color-stabilizing properties of a color-stable SAP composition of the present invention, comparative accelerated storage tests were performed. In one test, color-stable SAP compositions of the present invention (containing 0.5 mole % sodium sulfate and 0.5 mole % sodium hypophosphite) were compared to standard, commercial poly(acrylic acid) SAPs (DN about 70%).

This accelerated storage test was performed at 60° C. and 75% relative humidity over a six-month period. The test samples were observed visually for a color change. The color-stable SAP compositions of the present invention retained a clean white color over the six-month test period. The commercial SAPs changed color from white to honey brown.

Color measurements also were made on the test samples. In this test, Hunter Color 60 (HC60) measurements were made using a Gretag Macbeth Color-Eye 2180, available from Gretag-Macbeth, New Windsor, N.Y. The HC60 value is a standard measurement well known to persons skilled in the art. The HC60 value is an overall measure of color, and is calculated as: HC60=L-3b. In this test, an "L" value is a brightness number and a "b" value is an indication of yellowness. Accordingly, as the "b" value (yellowness) increases, the HC60 value decreases. A decreasing HC60 value indicates a color change from white to yellow to brown.

The three commercial SAPs had an initial HC60 value of 61.7, 56.6, and 58.0, respectively. After a six-month accelerated storage test, the commercial SAPs had an HC60 value of 43.5, 36.8, and 44.8, respectively. The large decrease in HC60 values illustrates a substantial degradation in color of the SAPs. The color degradation was sufficiently large such that articles containing the color-degraded SAP would not be acceptable to consumers.

In contrast, three color-stable SAP compositions of the present invention were subjected to an identical accelerated storage stability test. Each composition contained 0.5 mole % of the polyvalent metal salt (magnesium sulfate) and 0.5 mole % of the inorganic reducing agent (sodium hypophosphite). The three color-stable compositions of the present invention exhibited an initial HC60 value of 55.6, 57.8, and 62.8. After the six-month accelerated storage test, the compositions had an HC60 value of 56.5, 58.2, and 59.1, respectively. Accordingly, articles containing a color-stable SAP composition of the present invention remain acceptable to consumers at least over the expected life of the article.

A second accelerated storage test was conducted on diapers incorporating a color-stable SAP composition of the present invention. The storage test was conducted at 60° C. and 90% relative humidity. In this comparative test, three individual portions of an SAP sample were tested for color degradation using a Gardner Comparator 2000, available from Paul N. Gardner, Inc., Pompano Beach, Fla. Gardner color measurements are standard, and well known in the industry. One portion of the SAP sample contained an inorganic reducing agent and a metal salt. The second portion contained an inorganic reducing agent, but was free of a metal salt. The third portion contained neither an inorganic reducing agent nor a metal salt. Each portion of the SAP sample was incorporated into a different diaper.

The test results for two different SAP polymers are summarized in the following table:

| SAP Sample | Treatment | Time to Discolor to Gardner >6[1)] |
|---|---|---|
| 1 | None | 1.5 weeks |
| 1 | 0.65 mol % magnesium sulfate and 0.65 mol % sodium hypophosphite | 3.0 weeks |
| 1 | 1.57 mol % sodium hypophosphite | 8.0 weeks |
| 2 | None | 1.5 weeks |
| 2 | 0.65 mol % magnesium sulfate and 0.65 mol % sodium hypophosphite | 4.5 weeks |
| 2 | 1.57 mol % sodium hypophosphite | 8.0 weeks |

[1)]all samples had an initial Gardner Color of 0–1.

SAP Sample 1 was sodium polyacrylate particles neutralized about 75%, and surface crosslinked with 600 ppm ethylene glycol diglycidyl ether. The sodium hypophosphite and magnesium sulfate were applied to the surface of the SAP particles. SAP Sample 2 is similar to SAP Sample 1, except the sodium polyacrylate is neutralized about 60%. SAP Sample 2 is treated identically to SAP Sample 1.

The foregoing description is given for clearness of understanding only, and no unnecessary limitations should be understood therefrom, as modifications within the scope of the invention can be apparent to those skilled in the art.

What is claimed is:

1. A color-stable superabsorbent polymer composition comprising (a) a superabsorbent polymer, said superabsorbent polymer comprising a polymerized $\alpha,\beta$-unsaturated carboxylic acid or salt thereof, (b) about 0.5 to about 5 mole % of an inorganic reducing agent selected from the group consisting of a hypophosphite salt, a phosphite salt, and mixtures thereof, and (c) 0 to about 5 mole % of a water-soluble metal salt selected from the group consisting of an alkali metal salt, an alkaline earth metal salt, a metal salt having a polyvalent cation of valence II, III, or IV, and mixtures thereof, based on the amount of superabsorbent polymer in the composition.

2. The composition of claim 1 comprising about 0.05 to about 3 mole % of the metal salt.

3. The composition of claim 2 wherein the metal salt and reducing agent are present in a mole ratio of about 3:1 to about 1:3.

4. The composition of claim 1 wherein the $\alpha,\beta$-unsaturated carboxylic acid is selected from the group consisting of acrylic acid, methacrylic acid, ethacrylic acid, $\alpha$-chloroacrylic acid, $\alpha$-cyanoacrylic acid, $\beta$-methylacrylic acid, $\alpha$-phenylacrylic acid, $\beta$-acryloxypropionic acid, sorbic acid, $\alpha$-chlorosorbic acid, angelic acid, cinnamic acid, p-chlorocinnamic acid, $\beta$-stearylacrylic acid, itaconic acid, citraconic acid, mesaconic acid, glutaconic acid, aconitic acid, maleic acid, fumaric acid, tricarboxyethylene, maleic anhydride, and mixtures thereof.

5. The composition of claim 1 wherein the $\alpha,\beta$-unsaturated carboxylic acid has a degree of neutralization of about 50 to about 100.

6. The composition of claim 1 wherein the superabsorbent polymer is selected from the group consisting of polyacrylic acid, a starch-acrylic acid graft copolymer, an ethylene-maleic anhydride copolymer, an isobutylene-maleic anhydride copolymer, and mixtures thereof.

7. The composition of claim 1 wherein the superabsorbent polymer comprises an acidic superabsorbent polymer and a basic superabsorbent polymer.

8. The composition of claim 1 wherein the metal salt has a cation selected from the group consisting of salt of magnesium, calcium, aluminum, sodium, potassium, lithium, zinc, titanium, tin, bismuth, antimony, cerium, cobalt, lead, barium, manganese, iron, nickel, copper, and mixtures thereof.

9. The composition of claim 8 wherein the cation comprises magnesium.

10. The composition of claim 8 wherein the metal salt has an anion selected from the group consisting of sulfate, phosphate, acetate, lactate, and mixtures thereof.

11. The composition of claim 1 wherein the metal salt has a water solubility of at least about 3 grams in 100 milliliters of water at standard temperature and pressure.

12. The composition of claim 1 wherein the metal salt and reducing agent each are present, individually, in an amount of about 0.5 to about 3 mole %.

13. The composition of claim 1 wherein the metal salt and reducing agent each are present, individually, in an amount of about 0.65 to about 2 mole %.

14. The composition of claim 1 wherein the composition, after storage for six months at 60° C. and 75% relative humidity, exhibits a decrease in Hunter Color 60 color value of less than about 8 units.

15. The composition of claim 1 wherein the composition, after storage for six months at 60° C. and 75% relative humidity, exhibits a decrease in Hunter Color 60 color value of less than about 5 units.

16. The composition of claim 1 wherein the composition, after incorporation into a diaper and storage of the diaper for eight weeks at 60° C. and 95% relative humidity, exhibits a color change of less than 10 Gardner units.

17. An article comprising the color-stable superabsorbent polymer composition of claim 1.

18. The article of claim 17 selected from the group consisting of a diaper and a catamenial device.

19. A method of preventing discoloration of superabsorbent polymer particles comprising applying about 0.5 to about 5 mole % of an inorganic reducing agent selected from the group consisting of a hypophosphite salt, a phosphite salt, and mixtures thereof and 0 to about 5 mole % of a water-soluble metal salt selected from the group consisting of an alkali metal salt, an alkaline earth metal salt, a metal salt having a polyvalent cation of valence II, III, or IV, and mixtures thereof to a surface of the particles, to prevent an observable change in color of the particles after six months of storage at 60° C. and 75% humidity, wherein said superabsorbent polymer particles comprise a polymerized $\alpha,\beta$-unsaturated carboxylic acid or salt thereof.

20. A color-stable superabsorbent polymer composition comprising (a) a superabsorbent polymer, (b) about 0.5 to about 5 mole % of an inorganic reducing agent selected from the group consisting of a hypophosphite salt, a phosphite salt, and mixtures thereof, and (c) 0 to about 5 mole % of a water-soluble metal salt selected from the group consisting of an alkali metal salt, an alkaline earth metal salt, a metal salt having a polyvalent cation of valence II, III, and IV, and mixtures thereof, based on the amount of superabsorbent polymer in the composition, said superabsorbent polymer selected from the group consisting of a poly(vinylamine), a poly (dialkylaminoalkyl (meth)acrylamide), a polyethylenimine, a poly(allylamine), a poly (allylguanidine), a poly(dimethyldiallylammonium hydroxide), a quaternized polystyrene derivative, a guanidine-modified polystyrene, a quaternized poly ((meth)acrylamide), a poly(vinylguanidine), and salts and mixtures thereof.

* * * * *